(12) United States Patent
Spirio et al.

(10) Patent No.: US 9,012,404 B2
(45) Date of Patent: Apr. 21, 2015

(54) COMPOSITIONS AND METHODS FOR CARDIAC TISSUE PROTECTION AND REGENERATION

(75) Inventors: Lisa Spirio, Lexington, MA (US); Zen Chu, Cambridge, MA (US)

(73) Assignee: 3D Matrix, Inc., Cambridge, MA (US)

( * ) Notice: Subject to any disclaimer, the term of this patent is extended or adjusted under 35 U.S.C. 154(b) by 754 days.

(21) Appl. No.: 12/518,624

(22) PCT Filed: Dec. 11, 2007

(86) PCT No.: PCT/US2007/025271
§ 371 (c)(1),
(2), (4) Date: Aug. 12, 2009

(87) PCT Pub. No.: WO2008/073395
PCT Pub. Date: Jun. 19, 2008

(65) Prior Publication Data
US 2010/0143504 A1 Jun. 10, 2010

Related U.S. Application Data

(60) Provisional application No. 60/869,437, filed on Dec. 11, 2006.

(51) Int. Cl.
*A61K 38/00* (2006.01)
*A61P 9/00* (2006.01)
*A61K 38/10* (2006.01)

(52) U.S. Cl.
CPC ...................................... *A61K 38/10* (2013.01)

(58) Field of Classification Search
CPC ............................ A61K 38/10; A61K 2300/00
See application file for complete search history.

(56) References Cited

U.S. PATENT DOCUMENTS

| 5,670,483 | A | 9/1997 | Zhang et al. | |
|---|---|---|---|---|
| 7,429,567 | B2 * | 9/2008 | Lee et al. | 514/1.1 |
| 7,449,180 | B2 * | 11/2008 | Kisiday et al. | 424/93.7 |
| 2004/0242469 | A1 * | 12/2004 | Lee et al. | 514/12 |
| 2005/0181973 | A1 * | 8/2005 | Genove et al. | 514/2 |
| 2006/0084607 | A1 | 4/2006 | Spirio et al. | |
| 2006/0148703 | A1 * | 7/2006 | Lee et al. | 514/12 |

FOREIGN PATENT DOCUMENTS

| WO | 2005014615 A2 | 2/2005 |
|---|---|---|
| WO | 2006073889 A2 | 7/2006 |
| WO | 2006116524 A1 | 11/2006 |

OTHER PUBLICATIONS

Davis M.E., et al, "Local Myocardial Insulin-like Growth Factor 1 (IGF-1) Delivery with Biotinylated Peptide Nanofibers Improves Cell Therapy for Myocardial Infarction," Pro Natl Acad Sci U.S.A. 103, pp. 8155-8160, 2006.
Davis, M.E., et al, "Injectable Self-assembling Peptide Nanofibers Create Intramyocardial Microenvironments for Endothelial Cells," Circulation 111, pp. 442-450, 2005.
Holmes, T.C., et al, "Extensive Neurite Outgrowth and Active Synapse Formation on Self-assembling Peptide Scaffolds," Proc Natl Acad Sci U.S.A 97, pp. 6728-6733, 2000.
Hsieh, P.C., et al, "Controlled Delivery of PDGF-BB for Myocardial Protection Using Injectable Self-assembling Peptide Nanofibers," J Clin Invest 116, pp. 237-248, 2006.
Hsieh, Patrick C H et al, "Local Controlled Intramyocardial Delivery of Platelet-derived Growth Factor Improves Postinfarction Ventricular Function without Pulmonary Toxicity," Circulation, Aug. 15, 2006, vol. 114, No. 7, pp. 637-644.
Assmus et al., "Transcoronary transplantation of progenitor cells after myocardial infarction," N. Engl. J. Med. 355:1222-1232 (2006).
Braunwald et al., "Congestive heart failure: fifty years of progress," Circulation 102: IV14-23, 2000.
Brunner et al., "Attenuation of myocardial ischemia/reperfusion injury in mice with myocyte-specific overexpression of endothelial nitric oxide synthase," Cardiovasc. Res. 57:55-62, 2003.
Chien, "Lost and found: cardiac stem cell therapy revisited," J. Clin. Invest. 116: 1838-1840, 2006.
Chung et al., "Atrial and ventricular echocardiographic correlates of the extent of pulmonary embolism in the elderly," J. Am. Soc. Echocardiogr. 19:347-353, 2006.
Darland et al., "Cell-cell interactions in vascular development," Curr. Top. Dev. Biol. 107-149, 2001.
Engel et al., "FGF1/p38 Map kinase inhibitor therapy induces cardiomyocyte mitosis, reduces scarring, and rescues function after myocardial infarction," Proc. Natl. Acad. Sci USA 103:15546-15551, 2006.
Genove, E., et al, "The Effect of Functionalized Self-assembling Peptide Scaffolds on Human Aortic Endothelial Cell Function," Biomaterials 16, pp. 3341-3351, 2005.
Hiramatsu et al., "Effects of endothelin-1 and L-arginine after cold ischemia in lamb hearts," Ann. Thorac Surg. 61: 36-40; discussion 40-31, 1996.
Hoch et al., "Roles of PDGF in animal development," Development, 13:4769-4784, 2003.
Jugdutt, Ventricular remodeling after infaction and extracellular collagen matrix: when is enough enough?, Circulation, 108:1395-1403.
Narmoneva et al., "Endothelial cells promote cardiac myocyte survival and spatial reorganization: implications for cardiac regeneration," Circulation, 110:962-968, 2004.
Okonski et al., "Effect of L-arginine on oxygen consumption and haemodynamic function of rat's heart exposed to cold cardioplegic ischaemia and reperfusion," Ann. Transplan. 7:28-31, 2002.
Pfeffer et al., "Ventricular remodeling after myocardial infarction. Experimental observations and clinical implications," Circulation 81:1161-1172, 1990.

(Continued)

*Primary Examiner* — Thomas S Heard
(74) *Attorney, Agent, or Firm* — Lando & Anastasi, LLP (57) ABSTRACT

In various aspects the present inventions provide compositions and methods for treatment of cardiac conditions. In various embodiments, the present inventions provide methods for treating a cardiac condition comprising the step of administering in a therapeutically effective amount the substantially cell free solution of an amphiphilic self-assembling peptide to a site of cardiac tissue that has been injured due to one or more of atrial fibrillation, acute myocardial infarction; valve disease, pericardial disease, congenital heart disease, congestive heart failure, and embolism.

7 Claims, 3 Drawing Sheets

(56) References Cited

OTHER PUBLICATIONS

Saint John-Sutton et al., "Left ventricular remodeling after myocardial infaction: pathophysiology and therapy," Circulation, 101:2981-2988, 2000.

Stone et al., "Comparison of angioplasty with stenting, with or without abciximab, in acute myocardial infarction," N. Engl. J. Med. 346:957-966, 2002.

Thijssen et al., "Temporal and spatial variations in structural protein expression during the progression from stunned to hibernating myocardium," Circulation, 110:3313-3321.

Zhang, S., et al, "RO, Su X, and Rich, A. Self-complementary Oligopeptide Matrices Support Mammalian Cell Attachment," Biomaterials 18, pp. 1385-1393, 1995.

Zhang, S., et al, "Self-Assembling Nanofiber Scaffolds," In: Scaffolding in Tissue Engineering, Edited by Peter Ma and Jennifer Elisseeff, pp. 217-240, 2005.

* cited by examiner

COMPOSITIONS AND METHODS FOR CARDIAC TISSUE PROTECTION AND REGENERATION

This application claims the benefit under 35 U.S.C. §371 of International Application No. PCT/US07/025271 filed Dec. 11,2007 which claims priority to United States Provisional Patent Application No. 60/869,437, filed Dec. 11, 2006; the entire contents of each of which is hereby incorporated herein by reference.

INTRODUCTION

Chronic heart failure is common and increasing in prevalence (1) and ischemic heart disease is the leading cause of heart failure. Acute myocardial infarction (AMI) commonly known as a heart attack occurs when the blood supply to the heart is disrupted, causing necrosis or death of heart tissue. AMI is a medical emergency and is a leading cause of death for both men and women all over the world. Despite current medical, percutaneous interventional and surgical myocardial reperfusion strategies (2, 10, 11), there is much room for improvement.

The clinical presentation of patients with AMI ranges from mild chest pain to cardiogenic shock or sudden cardiac death. Treatment may be with medication (thrombolysis), angioplasty or bypass surgery. Medicinal treatments can include aspirin, thrombolytic agents (streptokinase, urokinase, alteplase (recombinant tissue plasminogen activator, rtPA), and reteplase), herapin, beta-blockers, and ACE inhibitors. The goal of immediate treatment is restoration of normal blood flow in the coronary arteries and improved tissue perfusion. This may also be accomplished with intravenous thrombolytic therapy or direct angioplasty. Clinical trials have shown that direct percutaneous transluminal coronary angioplasty (PTCA) restores flow most effectively and is the treatment of choice when performed by experienced clinicians.

Lack of blood supply or ischemia in the heart is the central issue in AMI, however when blood flow returns reperfusion injury can also occur. Reperfusion injury refers to the damage to tissue when blood supply returns to that tissue after a period of ischemia. The damage of reperfusion injury is partly due to the inflammatory response in the damaged tissue. When blood flow resumes, white blood cells carried to the ischemic area release a host of inflammatory factors such as interleukins as well as the generation of free radicals. The restoration of blood flow also causes damage to cell proteins, DNA and plasma membranes via the reintroduction of oxygen and the damage to cellular plasma membranes causes the release of additional free radicals. Free radicals are also believed to act indirectly to stimulate apoptotic responses in damaged tissues.

In addition, post-infarction ventricular remodeling results from net loss of cardiomyocytes (19) and techniques to improve cell viability and/or recruitment to the infarct zone could be beneficial in the recovery of cardiac contractility.

The early promise of progenitor cell transplantation for cardiac repair and regeneration, however, has been tempered by ambiguous clinical trial data showing minimal recovery of left ventricular contractility (3% improvement in left ventricular ejection fraction in treated versus control groups), short-lived improvement (no difference between groups by 18 months) or no difference at all. Furthermore, studies have shown that after delivery by intracoronary infusion, few of the transplanted cells are retained in the heart by 48 hours (4).

SUMMARY

The present inventions provide, in various aspects, methods for treating a cardiac condition using a substantially cell free biocompatible and biodegradable synthetic self-assembling peptide (SAP) scaffold material termed CardioMatrix. The inventors have discovered that purified self-assembling peptides can be fashioned into injectable and implantable gels suitable for use in a number of cardiac applications. The CardioMatrix materials and methods can be used to treat a wide range of cardiac tissue related conditions including, but not limited to, AMI, valve disease, pericardial disease, congenital heart disease, and congestive heart failure. For example, in various embodiments, the present inventions provide a therapeutic benefit by decreasing the extent of MI and reperfusion injuries after CardioMatrix injection.

As used herein, the term "CardioMatrix" refers to SAP comprised of a RADARADARADARADA sequence (SEQ. ID NO. 1).

As used herein, the term "cardiac condition" includes cardiac conditions, diseases, injuries, etc. As used herein "cardiac conditions" include, but are not limited to, AMI, valve disease, pericardial disease, congenital heart disease, and congestive heart failure.

In various embodiments, the present inventions provide methods for treating cardiac tissue comprising injecting into the tissue to be treated a substantially cell free solution containing greater than about 1% CardioMatrix by weight, and preferably greater than about 3% CardioMatrix by weight. In various embodiments, the solution comprises a sucrose solution containing a physiologically acceptable concentration of sucrose, e.g., a 10% by weight sucrose solution. The solution can contain one or more acceptable buffers to bring the solution to a physiological acceptable pH (e.g., pH of about 7 to about 8.5) prior to introducing the CardioMatrix solution into a subject. In various embodiments, these methods of treatment provide treatment, at least in part, via one or more of: local delivery of NO formed from LA, and promote formation of nitric oxide (NO) in response to physiological and/or pathological stimuli by CardioMatrix.

In various embodiments, the present inventions provide methods for treating an infarct comprising injecting into an infarct a substantially cell free solution containing greater than about 1% CardioMatrix by weight, and preferably greater than about 3% CardioMatrix by weight. In various embodiments, the solution comprises a sucrose solution containing a physiologically acceptable concentration of sucrose, e.g., a 10% by weight sucrose solution. The solution can contain one or more acceptable buffers to bring the solution to a physiological acceptable pH (e.g., pH of about 7 to about 8.5) prior to introducing the CardioMatrix solution into a subject.

In various embodiments, the present inventions provide methods for the treatment of one or more of hypertension, septic shock, neuro-degeneration, arthritis, and asthma by injection into a tissue to be treated a substantially cell free solution containing greater than about 1% CardioMatrix by weight (and preferably greater than about 3% CardioMatrix by weight) that provides treatment, at least in part, via one or more of: local delivery of NO formed from LA, and promote formation of nitric oxide (NO) in response to physiological and/or pathological stimuli by CardioMatrix. Accordingly, in various embodiments, the present inventions provide methods for the treatment of one or more of hypertension, septic shock, neuro-degeneration, arthritis, and asthma using local administration of a LA containing CardioMatrix.

In various aspects, the present methods comprise providing a cardio-protective and/or cardio-regenerative effect by local administration of a substantially cell free solution containing greater than about 1% CardioMatrix by weight, and preferably greater than about 3% CardioMatrix by weight.

The foregoing and other aspects, embodiments, and features of the present inventions can be more fully understood from the following description and drawings.

BRIEF DESCRIPTION OF THE DRAWINGS

FIG. 2 Presents information on the histopathological scoring and photographical analysis of rat heart with vehicle alone (a) and 3% CardioMatrix (b). Scoring for infarct size or wall thinning-only the anterior region of the heart was scored as follows: 0-0% or no areas scoring positive for infarct or thinning, 1-25% of the area affected, termed mild, 2-50% of the area affected-moderate, 3 or 4 (75-100%) areas affected-severe. (a) Photograph of vehicle control shows a large area of the anterior wall was infarcted (areas 1-3 or 75% of the anterior region). This same slice also shows severe thinning whereas the 3% CardioMatrix shows little thinning. (b) Photograph of the 3% CardioMatrix treated animal shows just 25% of the anterior region showing infarct. Additionally, there is little wall thinning in this section for the 3% SAP treated animal.

DETAILED DESCRIPTION

In various aspects, the present inventions provide injectable CardioMatrix, comprised of a self-assembling RADARADARADARADA sequence, capable of forming nanofiber scaffolds that promote increasing one or more of cardiac cell preservation and cardiac cell recruitment. In various aspects, the present inventions provide methods of treatment comprising local myocardial injection of a CardioMatrix material. In various embodiments, the methods promote improved recovery of ventricular contractility after myocardial infarction. In various embodiments, provided are methods for treating one or more of AMI, valve disease, pericardial disease, congenital heart disease, and congestive heart failure, by local myocardial injection of a CardioMatrix material. In various embodiments, provided are methods for treating one or more of hypertension, septic shock, neuro-degeneration, arthritis, and asthma, using local administration of a LA containing CardioMatrix.

CardioMatrix Materials & Solutions

The following definitions may be useful in understanding SAPs, and SAP structures, and the CardioMatrix material.

By "scaffold" is meant a three-dimensional structure capable of supporting cells. Cells may be encapsulated by the scaffold or may be disposed in a layer on a surface of the scaffold. The beta-sheet secondary structure of the scaffold may be confirmed using standard circular dichroism to detect an absorbance minimum at approximately 218 nm and a maximum at approximately 195 nm. The scaffold is formed from the self-assembly of peptides that may include L-amino acids, D-amino acids, natural amino acids, non-natural amino acids, or a combination thereof. If L-amino acids are present in the scaffold, degradation of the scaffold produces amino acids which may be reused by the host tissue. It is also contemplated that the peptides may be covalently linked to a compound, such as a chemoattractant or a therapeutically active compound. The peptides may be chemically synthesized or purified from natural or recombinant sources, and the amino- and carboxy-termini of the peptides may be protected or not protected. The peptide scaffold may be formed from one or more distinct molecular species of peptides which are complementary and structurally compatible with each other. Peptides containing mismatched pairs, such as the repulsive pairing of two similarly charged residues from adjacent peptides, may also form scaffolds if the disruptive force is dominated by stabilizing interactions between the peptides. Scaffolds are also referred to herein as peptide structures, peptide hydrogel structures, peptide gel structures, or hydrogel structures.

By "complementary" is meant capable of forming ionic or hydrogen bonding interactions between hydrophilic residues from adjacent peptides in the scaffold; for example, each hydrophilic residue in a peptide either hydrogen bonds or ionically pairs with a hydrophilic residue on an adjacent peptide or is exposed to solvent.

By "structurally compatible" is meant capable of maintaining a sufficiently constant intrapeptide distance to allow scaffold formation. In certain embodiments of the invention the variation in the intrapeptide distance is less than 4, 3, 2, or 1 angstroms. It is also contemplated that larger variations in the intrapeptide distance may not prevent scaffold formation if sufficient stabilizing forces are present. This distance may be calculated based on molecular modeling or based on a simplified procedure that has been previously reported (U.S. Pat. No. 5,670,483). In this method, the intrapeptide distance is calculated by taking the sum of the number of unbranched atoms on the side-chains of each amino acid in a pair. For example, the intrapeptide distance for a lysine-glutamic acid ionic pair is 5+4=9 atoms, and the distance for a glutamine-glutamine hydrogen bonding pair is 4+4=8 atoms. Using a conversion factor of 3 angstroms per atom, the variation in the intrapeptide distance of peptides having lysine-glutamic acid pairs and glutamine-glutamine pairs (e.g., 9 versus 8 atoms) is 3 angstroms.

The term "pure" is used to indicate the extent to which the peptides described herein are free of other chemical species, including deletion adducts of the peptide in question and peptides of differing lengths.

The term "biologically active agent" is used to refer to agents, compounds, or entities that alter, inhibit, activate, or otherwise affect biological or biochemical events. Such agents may be naturally derived or synthetic. Biologically active agents include classes of molecules (e.g., proteins, amino acids, peptides, polynucleotides, nucleotides, carbohydrates, sugars, lipids, nucleoproteins, glycoproteins, lipoproteins, steroids, growth factors, chemoattractants, etc.) that are commonly found in cells and tissues, whether the molecules themselves are naturally-occurring or artificially created (e.g., by synthetic or recombinant methods). Biologically active agents also include drugs, for example, anti-cancer substances, analgesics, and opioids. Preferably, though not necessarily, the drug is one that has already been deemed safe and effective for use by the appropriate governmental agency or body. For example, drugs for human use listed by the FDA under 21 C.F.R. §§330.5, 331 through 361, and 440 through 460; drugs for veterinary use listed by the DA under 21 C.F.R. §§500 through 589, incorporated herein by reference are all considered acceptable for use in accordance with the present invention. Additional exemplary biologically active agents include but are not limited to anti-AIDS substances, anti-cancer substances, immunosuppressants (e.g., cyclosporine), anti-viral agents, enzyme inhibitors, neurotoxins, hypnotics, anti-histamines, lubricants, tranquilizers, anti-convulsants, muscle relaxants and anti-Parkinson agents, anti-spasmodics and muscle contractants including channel blockers, miotics and anti-cholinergics, anti-glaucoma compounds, anti-parasite, anti-protozoal, and/or anti-fungal compounds, modulators of cell-extracellular matrix interactions including cell growth inhibitors and anti-adhesion molecules, vasodilating agents, inhibitors of DNA, RNA or protein synthesis, anti-hypertensives, anti-pyretics, steroidal and non-steroidal anti-inflammatory agents, anti-angiogenic factors, anti-secretory factors, anticoagulants and/or antithrombotic agents, local anesthetics, ophthalmics, prostaglandins, targeting agents, neurotransmitters, proteins, cell response modifiers, and vaccines.

As used herein, a hydrogel such as a peptide hydrogel is "stable with respect to mechanical or physical agitation" if, when subjected to mechanical agitation, it substantially retains the physical properties (such as elasticity, viscosity, etc.), that characterized the hydrogel prior to physical agitation. The hydrogel need not maintain its shape or size and may fragment into smaller pieces when subjected to mechanical agitation while still being termed stable with respect to mechanical or physical agitation. The term "stable" does not have this meaning except when used with this phrase.

As used herein, the term "nanofiber" refers to a fiber having a diameter of nanoscale dimensions. Typically a nanoscale fiber has a diameter of 500 nm or less. According to certain embodiments of the invention a nanofiber has a diameter of less than 100 nm. According to certain other embodiments of the invention a nanofiber has a diameter of less than 50 nm. According to certain other embodiments of the invention a nanofiber has a diameter of less than 20 nm. According to certain other embodiments of the invention a nanofiber has a diameter of between 10 and 20 nm. According to certain other embodiments of the invention a nanofiber has a diameter of between 5 and 10 nm. According to certain other embodiments of the invention a nanofiber has a diameter of less than 5 nm.

The term "nanoscale environment scaffold" refers to a scaffold comprising nanofibers. According to certain embodiments of the invention at least 50% of the fibers comprising the scaffold are nanofibers. According to certain embodiments of the invention at least 75% of the fibers comprising the scaffold are nanofibers. According to certain embodiments of the invention at least 90% of the fibers comprising the scaffold are nanofibers. According to certain embodiments of the invention at least 95% of the fibers comprising the scaffold are nanofibers. According to certain embodiments of the invention at least 99% of the fibers comprising the scaffold are nanofibers. Of course the scaffold may also comprise non-fiber constituents, e.g., water, ions, growth and/or differentiation-inducing agents such as growth factors, therapeutic agents, or other compounds, which may be in solution in the scaffold and/or bound to the scaffold.

As used herein, the term "effective amount" includes an amount effective, at dosages and for periods of time necessary, to achieve the desired result. An effective amount may vary according to factors such as the disease state, age, and weight of the subject. Dosage regimens may be adjusted to provide the optimum therapeutic response. An effective amount is also one in which any toxic or detrimental effects (e.g., side effects) are outweighed by the therapeutically beneficial effects.

CardioMatrix is a self-assembling peptide (SAP) containing the sequence RADARADARADARADA and is a member of a class of peptide biomaterials that have been developed in the context of cell culture, stem cell biology and tissue engineering (24, 25). CardioMatrix sequences for use in the present inventions can also be modified to contain active sequences from various growth factors (eg. platelet-derived growth factor) and/or extracellular matrix proteins (eg. collagen, laminin) (10, 14). Examples of the preparation and characterization of SAPs can be found in U.S. Published Application Nos. 2004/0242469 and 2006/0084607, the entire contents of both of which are incorporated herein by reference. In various embodiments, the CardioMatrix material comprises purified amphiphilic peptides where the peptides are at least 75% pure, preferably at least 85% pure and more preferably at least 95% pure.

The CardioMAtrix material is used in the present inventions in the form of an injectable aqueous solution. The concentration of peptide chains in solution can be varied. In various embodiments, the concentration of the peptide chains in solution is one or more of: between about 1% and about 10% by weight; between about 3% and about 7% by weight; and between about 6% and about 10% by weight. In various embodiments, the concentration of the peptide chains in solution is one or more of: greater than about 2% by weight; greater than about 3% by weight; greater than about 4% by weight; greater than about 5% by weight; greater than about 6% by weight; greater than about 7% by weight; and greater than about 8% by weight. The CardioMatrix solutions are formulated to avoid osmotic shock to a subject tupon administration. In various embodiments, the CardioMatrix solutions are prepared using an about 10% sucrose solution. A CardioMatrix solution may have a shelf life of at least one year with or without added electrolyte.

The CardioMatrix solution can contain one or more acceptable buffers to bring the solution to a physiological acceptable pH (e.g., pH of about 7 to about 8.5) prior to introducing the solution into a subject.

The CardioMatrix solution is preferably sterilized prior to use in a subject. The CardioMatrix powder can be radiation sterilized, for example, by exposure to gamma radiation to about 35 Kgrey. CardioMatrix solutions can be made that are stable with respect to exposure to radiation and structural alterations upon exposure to sterilizing radiation.

The peptide chains in the CardioMatrix solution can be made to spontaneously self-assemble into scaffolds through electrostatic interactions. The self-assembled CardioMatrix peptide chains can form a hydrogel that remains ductile and amenable to flow upon application of an appropriate stimulus. In general, SAPs upon the introduction of millimolar amounts of monovalent cations, either through the addition of salt solution, cell culture media or injection of the material in-vivo, can undergo self-assembly into nanofibers, approximately 10 nm in diameter, which form well-ordered 3-dimensional porous scaffolds (13). The amphiphilic peptides' charge density, size and water-structuring abilities can mimic those of in-vivo extracellular matrix. The nanofiber density and average pore size, ~5-200 nm, correlate with the concentration of peptide solution that is used to produce the material.

The CardioMatrix solutions can be formed into a stable scaffold by exposure to a monovalent salt solution. Sufficient electrolyte is added to the solution to initiate self-assembly of the peptides into a beta-sheet macroscopic structure upon contact with tissue at the site of administration. In various embodiments, the concentration of the added electrolyte is at least 5, 10, 20, or 50 mM. Smaller concentrations, e.g., 0.1 to 1 mm, or larger concentrations can also be used. The choice of concentration depends partially on the desired ionic strength of the peptide gel and also affects the speed of gelation. Suitable electrolytes include, but are not limited to, $Li^+$, $Na^+$, $K^+$, and $Cs^+$. The electrolyte causes the peptide chains to self-assemble into a scaffold that is stable with respect to mechanical agitation.

In various embodiments, the present inventions provide a substantially cell free solution comprising an amphiphilic self-assembling peptide having the complementary components of providing a: 1) a suitable biological scaffold that creates a microenvironment niche for cardiac cell types, and 2) that the endogenous cardiac cells and/or engrafted cell population can rapidly integrate into the needed tissue (24, 25).

The CardioMatrix scaffold materials of the present inventions comprise a network of nanofibers with intervening spaces rather than a solid matrix, which can promote cell infiltration and cell-cell interactions to promote healing. In the methods of the present inventions, the introduction of the CardioMatrix material can be performed "cell-free," for example, the methods do not require the preparation of cells to be introduced into infarcted areas for the treatment of cardiac tissues.

It is believed, without being held to theory, that creation of an in-vivo like microenvironment, including an ECM component facilitates successful cell engraftment (7, 8, 9). The CardioMatrix materials of the present inventions provide, in various embodiments, appropriate three-dimensional architecture, promote signaling pathways influencing critical cell functions, such as proliferation, differentiation, and migration, or both (7-10, 14, 15). Furthermore, since the CardioMatrix solutions does not gel until it is administered, it could prevent back leakage of injected cells into the desired region—this technical advantage has proven to be extremely helpful in several pre-clinical studies conducted by the inventors.

The CardioMatrix solution of the present inventions is injectable, and can, in various embodiments, be used for localized drug delivery. For example, according to various embodiments, the CardioMatrix solution is used to deliver drugs directly to the heart for either short term therapy, long term therapy, or both. Accordingly, instead of repeated systemic administration, CardioMatrix containing the desired agent can be periodically delivered directly to a desired area of the heart. All concentrations of CardioMatrix solution are injectable with any size needle, even very fine gauge needles (30 gauge).

These CardioMatrix solutions, in various embodiments, can behave as a injection-molded material. The hydrogels passed through a needle fill a desired space with a single coherent bolus rather than a tangled, threaded mass. That is, the material assembles both at the scale of the individual peptide chains and on a macroscale as a gel. The CardioMatrix solutions can in various embodiments thus provide both an injectable material for ease of administration and a continuous fibrous network that facilitates cellular ingrowth and proliferation. A wide variety of devices can be used to deliver the injectable solutions including, but note limited, syringes, dual-chamber syringes, injection catheters, and delivery catheters.

These CardioMatrix solutions, in various embodiments, can behave as non-Newtonian fluids. For example, the solution can become more viscous over time. For example, a 3% solution could exhibit a yield stress of 20-30 Pa and a viscosity less than 40 cP about an hour after mixing, the yield stress could increase to 50-65 Pa after about 5-6 hours, and after about two weeks, the yield stress could increase to about 100-160 Pa, and the viscosity increased to less than 200 cP.

One or more biologically active agents (platelet rich plasma) for example, therapeutically active compounds or chemo-attractants, can be added to the CardioMatrix (10, 14). Growth factors alone or in combination with other biologically active agents such as cytokines (epidermal growth factor, nerve growth factor, transforming growth factor-alpha and beta, platelet-derived growth factor, insulin-like growth factor, vascular endothelial growth factor, etc.) can be added to the CardioMatrix material (10, 14). Drugs and growth factors each can be added in a similar fashion to CardioMatrix, for example, as follows: the desired drug or growth factor at 2× concentration is added to the sucrose vehicle solution, at a volume equal to that of sucrose vehicle solution, then mixed with CardioMatrix prior to injection.

Biocompatibility and toxicology tests on CardioMatrix of the present inventions, have shown that these materials, when implanted into animals or tested in vitro, are safe and biocompatible. We have also shown that when injected in vivo, CardioMatrix is degraded and excreted within 28 days. Lastly, hemocompatibility tests have shown that CardioMatrix in direct contact with blood and plasma do not initiate coagulation cascades that would be detrimental for many applications in vivo. Biocompatibility and toxicology test results are shown in Example 2.

Methods of Treatment

In various aspects, the present inventions provide methods of treatment comprising local injection of a substantially cell free CardioMatrix material into a tissue to be treated. In various embodiments the tissue to be treated comprises cardiac tissue, including but not limited to vascular, arterial, muscular, arterial lining, etc. tissues. In various embodiments, the substantially cell free material is injected as a solution containing greater than about 1% CardioMatrix by weight, and preferably greater than about 3% CardioMatrix by weight. In various embodiments, the present methods comprise providing a cardio-protective and/or cardio-regenerative effect by local administration of a substantially cell free solution containing greater than about 1% CardioMatrix by weight, and preferably greater than about 3% CardioMatrix by weight.

Acute and chronic changes in ventricular remodeling after AMI are important processes that effect cardiac function (16). AMI events lead to edema and inflammation in the heart which causes the infracted region to expand beyond the originally damaged area. The infarct expansion occurs 2-10 days after the event and causes necrosis not only in the original infracted zone but also in the expanded area (16). Additionally, "stunning" in the heart occurs immediately after ischemia and subsequent reperfusion while "hibernation" is a process by which the myocardium adapts to chronic ischemia which involves a metabolic switch to alternative types of energy consumption, typically in the form of anaerobic glycolysis (22). Infracted cardiac tissue can enter a "hibernating" state from a chronically "stunned" state and this transition correlates with a temporal and spatial variation in structural protein expression during the progression (23). Accordingly, in various aspects, the present inventions provide methods for providing a cardio-protective and/or cardio-regenerative effect by local administration of a substantially cell free solution containing greater than about 1% CardioMatrix by weight, and preferably greater than about 3% CardioMatrix by weight. In various embodiments, the treatment methods provide one or more of: controlling infarct size, reducing or preventing infarct expansion, and reducing ventricular wall stress.

For example, in various embodiments, a substantially cell free solution containing an amphiphilic self-assembling peptide can be used to create embolization. For example, the substantially cell free solution can be administered to (e.g., injected into) blood vessels around a tumor or vessels that have been cut during surgery to stop blood flow.

In various embodiments, the substantially cell free solution containing an amphiphilic self-assembling peptide can be injected into heart muscle to stimulate muscle production at thinning cardiac walls. Without being bound to theory, we believe that injection into certain tissue sites creates a permissive cavity for cell ingrowth and tissue development. The pH of the solution can be adjusted to further promote cell ingrowth and extracellular matrix production, and/or growth factors can be added to promote, e.g., specific cell behavior.

As used herein the terms, "treat," "treatment," "treating" and "therapy" are used interchangeably to refer to any method used to partially or completely alleviate, ameliorate, relieve, inhibit, delay onset of, reduce severity of and/or reduce incidence of one or more symptoms or features of a particular disease, disorder, injury and/or condition. For example, treatment may be administered to a subject who does not exhibit signs of a disease or condition and/or exhibits only early signs of the disease or condition; treatment may be administered to a subject who has suffer an injury (for example as a result of AMI); etc.

In various embodiments of the present inventions, the methods provide a CardioMatrix solution that treats the damaged tissue by keeping it in a stunned state until the edema and inflammation subside (19, 22). In various embodiments, the CardioMatrix solutions are employed as a bulking agent that protects the tissue from wall stress which would further compromises cardiac function and, for example, provide a biomechanical or biophysical protective effect towards the infracted tissue, promoting protection from further injury (19).

In various aspects, the present inventions provide methods of treatment comprising local myocardial injection of a CardioMatrix material. In various embodiments, the present inventions provide methods for treating an infarct comprising injecting into an infarct a substantially cell free solution containing greater than about 1% CardioMatrix by weight, and preferably greater than about 3% CardioMatrix by weight. In various embodiments, the solution comprises a sucrose solution containing a physiologically acceptable concentration of sucrose, e.g., a 10% by weight sucrose solution. The solution can contain one or more acceptable buffers to bring the solution to a physiologically acceptable pH (e.g., pH of about 7 to about 8.5) prior to introducing the CardioMatrix solution into a subject.

In various embodiments, the present inventions provide methods for the treatment of one or more of hypertension, septic shock, neuro-degeneration, arthritis, and asthma using local administration of a LA containing CardioMatrix. In various embodiments, treatment of one or more of hypertension, septic shock, neuro-degeneration, arthritis, and asthma is provided by injection into a tissue to be treated a substantially cell free solution containing greater than about 1% CardioMatrix by weight, and preferably greater than about 3% CardioMatrix by weight. In various embodiments, the treatment, increases the local delivery of NO to the treated tissue. In various embodiments, the treatment provides local delivery of NO formed from LA in the Cardiomatrix. In various embodiments, the CardioMatrix, promotes the formation of nitric oxide (NO) by the treated tissues and/or tissues in physiological communication with the treated tissues.

EXAMPLES

Example 1

CardioMatrix Studies: Ischemia-Reperfusion Rat Model

In this example, an ischemia-reperfusion rat model was used to test whether the use of local myocardial injection of CardioMatrix, improves ventricular remodeling after infarction, as measured by ventricular contractility and pathology assessments of infarct size and severity. In these examples, the introduction of the CardioMatrix material was performed "cell-free," that is, it did not use or require the preparation of cells to be introduced into the infarcted areas.

CardioMatrix Materials

CardioMatrix was prepared as follows: CardioMatrix powder was dissolved in vehicle control solution (10% sucrose) to produce the 1% and 3%, concentration by weight, solutions used in this example. The solution was substantially cell free. The solution was then transferred to a syringe for injection. A 10% sucrose solution was used as the control.

Surgery, AMI and Injection of CardioMatrix

Male Sprague Dawley rats, n=29, 240-300 g weight, had transmural ischemia created under general anesthesia (pentobarbital 0.06-0.10 mg/g ip). After intubation and midline sternotomy, the middle segment of the left anterior descending artery was ligated with a 7/0 suture and ischemia was confirmed by a pale discoloration of the myocardium in the distal left anterior descending artery territory. After 45 minutes, the suture was cut and removed. Two rats died while the artery was ligated.

The rats (n=27) were randomized to receive one of 3 materials: 3% CardioMatrix (3% CardioMatrix, 3DM Inc., Cambridge, Mass., USA), 1% CardioMatrix (1% CardioMatrix, 3DM Inc., Cambridge, Mass., USA) or vehicle control (CardioMatrix vehicle, 3DM, Inc., Cambridge, Mass., USA). After 3 minutes of anterior myocardial reperfusion, a total of 50 microliters of material was delivered into the infarcted myocardium with 3 injections into the territory of the distal left anterior descending artery. The sternotomy was then closed with 4/0 suture and the rats were allowed to recover.

Echocardiography

Transthoracic echocardiography was performed on the $3^{rd}$ day after surgery using a 13 MHz linear array ultrasound probe (Vivid 7, GE Medical Systems, Milwaukee, Wis., USA) after light sedation (ketamine, 0.05-0.10 mg/g ip). Left ventricular dimensions were measured from the parasternal short-axis M-mode tracings at the mid-ventricular level and the left ventricular ejection fraction (LVEF) was calculated with the Teich method (5). The measurements obtained from 2 consecutive tracings were averaged.

Echocardiography was repeated under light sedation on the $28^{th}$ day after surgery using the methods described previously. The rats were then anesthetized (sodium pentobarbital 0.10 mg/g ip), sacrificed and the hearts explanted for pathological assessment.

Pathology

Each heart was sliced into 5 concentric rings from apex to base. Each ring was assessed for presence or absence of infarction, wall thinning, fibrosis and inflammation. Only the anterior region of the heart where the infarct was created was scored for infarct severity or wall-thinning. The effects were scored as follows: 0-0% or no areas scoring positive for infarct or thinning, 1-25% of the area affected, termed mild, 2-50% of the area affected-moderate, 3 or 4 (75-100%) areas affected-severe. The investigators performing rat surgery, echocardiography and pathology assessment were blinded to which material the rat received.

All statistical analyses were performed using SPSS for Windows 10.0 (SPSS Inc, Chicago, USA). As data were parametric, they are expressed as mean±standard deviation with a 2-tailed p-value of 0.05 was considered significant. Categorical variables were compared with chi-squared and Fisher exact tests. Paired t-tests and independent t-tests were used to test for within subject and between subject differences.

Results

Echocardiography

Figure 1:
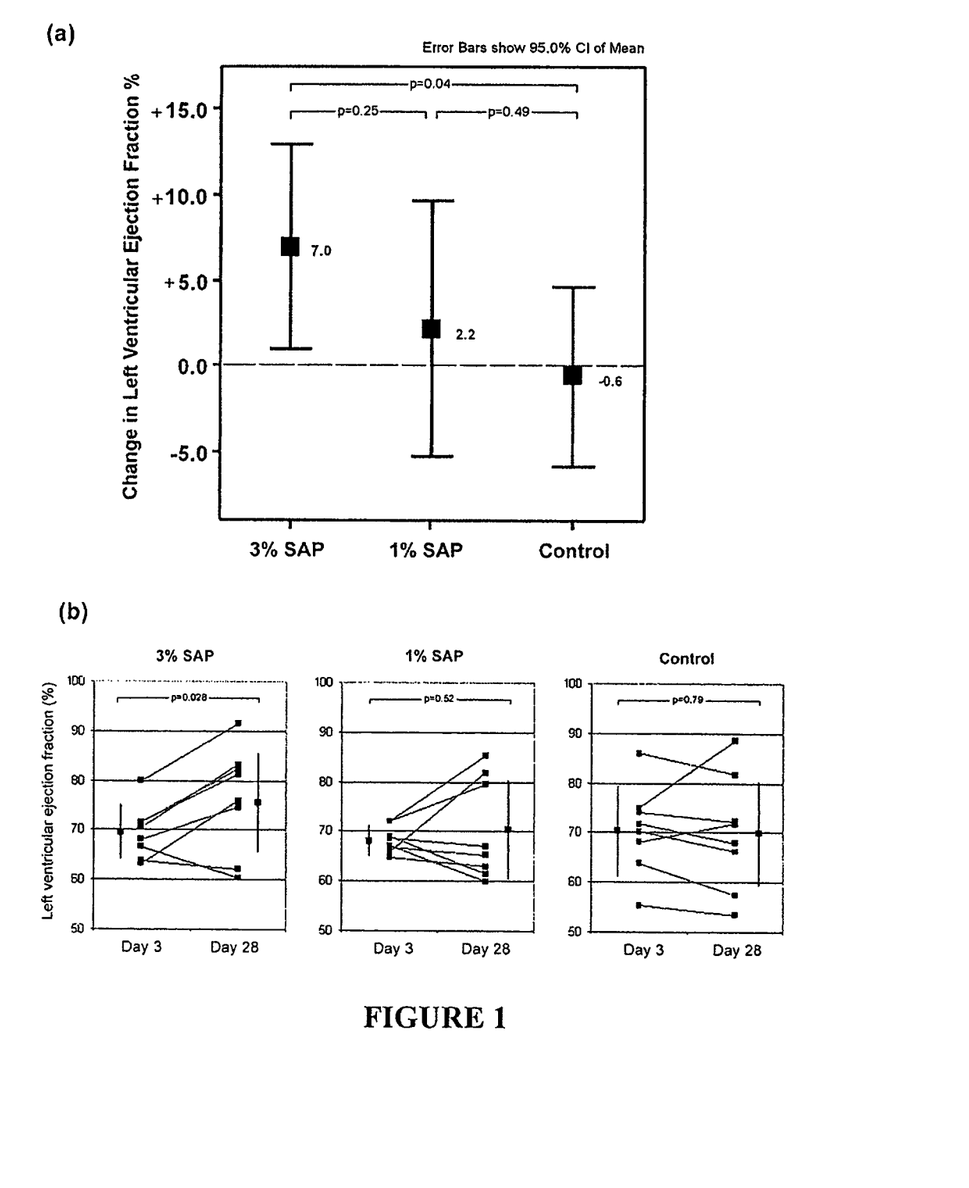
FIG. 1 Presents information on the change in Left Ventricular Ejection Fraction % between Day 3 and Day 28 post-ischemic-reperfusion (a) group totals and (b) per animal in each group. The 3% CardioMatrix group exhibits a statistically significant improvement over controls at day 28. LVEFs charted per animal at day 3 and day 28 demonstrate the trends in improvement of the 3% and 1% groups.

Of the 27 rats, 3 died (1 each from each group) before the second echocardiogram leaving 24 for analysis. Table 1 shows the LVID measurements in centimeters at days 3 and 28, the LVEFs in percentage at days 3 and 28, and the change in LVEF from days 3 and 28 for each of the 3 experimental groups. On day 3 post-ischemia-reperfusion, there was no difference in LVEF between the 3% CardioMatrix, 1% CardioMatrix and vehicle control groups (69.4±5.3%, 68.3±2.7% and 70.5±8.9%, respectively, p>0.50, Table 1) demonstrating that the infarcts were administered in a uniform fashion to all of the rats in the study.

studied individually, there also was statistically-significant improvement in the LVEFs from day 3 to day 28 for the 3% CardioMatrix group (69.4±5.3% versus 76.4±10.7%, mean change of 7.0±7.1%, p=0.028, Table 1, FIG. 1b) a positive trend in the 1% CardioMatrix group (68.3±2.7% versus 70.5±10.1%, mean change of 2.2±8.9%, p=0.52, Table 1, FIG. 1b) but not for the vehicle control group (70.5±8.9% versus 69.9±11.5%, mean change of −0.6±6.3%, p=0.79, Table 1, FIG. 1b). FIG. 1(b) also includes a representation of each of the groups plotted separately with each animal represented by a single line bounded by the measurements at day 3 and day 28. Of the 8 animals in each group, there was an improvement in LVEF in 6 rats in the 3% CardioMatrix group, 3 in the 1% CardioMatrix group and 2 in the vehicle control group (see FIG. 1(b)). Taken together, these calculations demonstrate that treatment with 3% CardioMatrix compared to the vehicle control shows statistically-significant enhancement of LVEF in rats that previously sustained an AMI event.

Pathology

Figure 2:
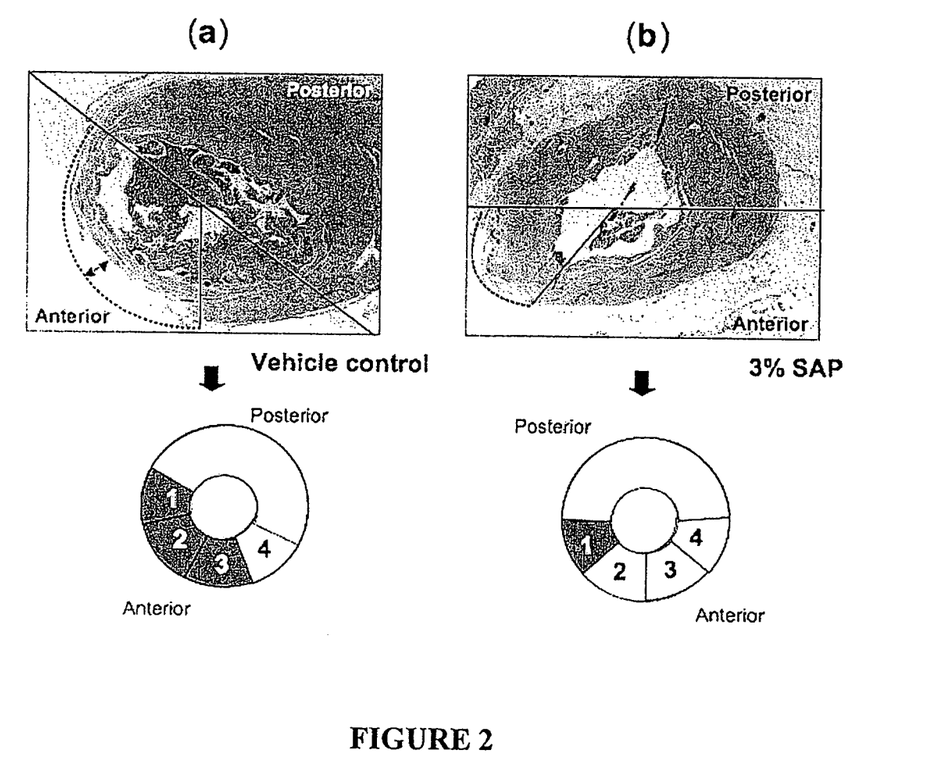

For each of the 24 rats that were sacrificed at 28 days, the hearts were cut into five sections and evaluated separately on a scale of 0-4 (0-no effect, 4-severe) for infarction size, wall thinning, fibrosis and inflammation. Examples of scoring for infarct are pictured in FIG. 2. In part a of FIG. 2, the vehicle control is shown to have an extensive area of infarction (75% of the anterior region of the heart) versus part b, the 3% CardioMatrix, which demonstrates a much smaller area of infarction (25% of the anterior region of the heart). The number of slices per rat with infarction, fibrosis, and inflammation were all similar in the 3% CardioMatrix, 1% CardioMatrix and the vehicle control groups (Table 1). The results were also

TABLE 1

Echocardiography results.

| I. Echocardiography | 3% CardioMatrix mean ± SD | 1% CardioMatrix mean ± SD | Control mean ± SD | 3% vs 1% p-value | 3% vs control p-value | 1% vs control p-value |
|---|---|---|---|---|---|---|
| 1. Day 3 LVIDd (cm) | 0.63 ± 0.06 | 0.69 ± 0.11 | 0.65 ± 0.11 | 0.15 | 0.62 | 0.42 |
| 2. Day 3 LVIDs (cm) | 0.41 ± 0.05 | 0.44 ± 0.08 | 0.42 ± 0.11 | 0.39 | 0.69 | 0.78 |
| 3. Day 3 LVEF (%) | 69.4 ± 5.3 | 68.3 ± 2.7 | 70.5 ± 8.9 | 0.60 | 0.77 | 0.51 |
| 4. Day 28 LVIDd (cm) | 0.74 ± 0.09 | 0.72 ± 0.15 | 0.72 ± 0.16 | 0.80 | 0.83 | 0.98 |
| 5. Day 28 LVIDs (cm) | 0.44 ± 0.11 | 0.47 ± 0.14 | 0.48 ± 0.16 | 0.61 | 0.60 | 0.95 |
| 6. Day 28 LVEF (%) | 76.4 ± 10.7 | 70.5 ± 8.9 | 69.9 ± 11.5 | — | — | — |
| 7. Change in LVEF % | +7.0 ± 7.1 | +2.2 ± 8.9 | −0.6 ± 6.3 | 0.25 | 0.04 | 0.49 |
| 8. Within group p-value (day 3 vs 28) | 0.028 | 0.52 | 0.79 | — | — | — |

The mean and SDs are calculated per parameter and the corresponding p-value calculated for each comparison. Additionally, the values shown in bold are pictured in FIG. 1.

Figure 3:
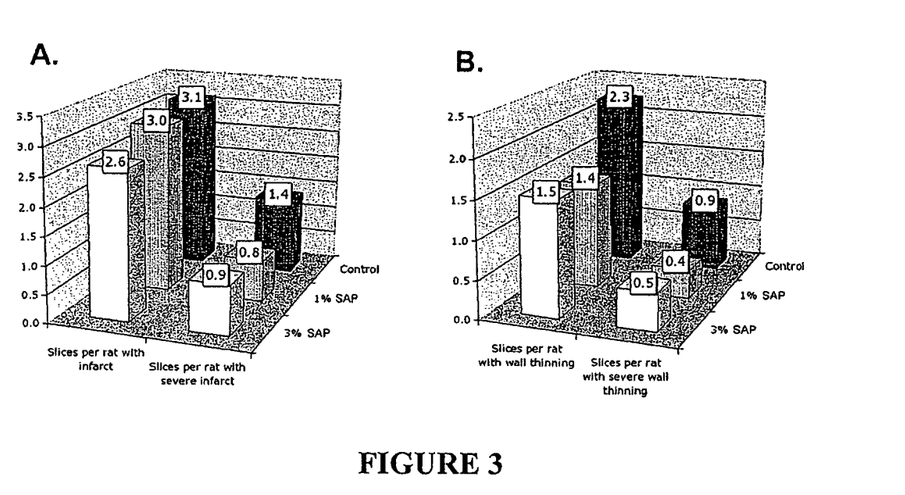
FIG. 3 Presents information on the CardioMatrix treatment reducing wall thinning area and severity. (A) Slices per rat with infarct and severe infarct comparing in animals receiving 3% CardioMatrix, 1% CardioMatrix and vehicle control. (B) Slices per rat with wall thinning and severe wall thinning in animals receiving 3% CardioMatrix, 1% CardioMatrix and vehicle control.

In order to determine the effects of CardioMatrix treatment on ventricular function in this rat model of AMI, p values were calculated comparing the treatments to each other (i.e., 3% CardioMatrix versus 1% CardioMatrix or control and 1% CardioMatrix versus control) and the p values comparing treatment within a single group (i.e., 3% CardioMatrix, 1% CardioMatrix or control at day 3 versus day 28) (FIG. 1). The corresponding p-values were calculated for the comparisons between 3% CardioMatrix versus 1% v (p=0.25), 3% CardioMatrix versus control (p=0.04) and 1% CardioMatrix versus control (p=0.49) (Table 1, line 7 in bold) and are shown in FIG. 1(a). The 3% CardioMatrix versus control p value of 0.04 demonstrates a statistically-significant improvement in the animals receiving 3% CardioMatrix compared to animals receiving the vehicle control. When each of the groups was tabulated separately as total cases and severe for each indication. We saw no differences in the amount of fibrosis or inflammation present when the groups compared to the other groups or within a single group (day 3 versus day 28 comparisons) (Table 2, lines 5 and 6). There were, however, positive trends for fewer slices per rat in the 3% and 1% CardioMatrix compared to vehicle control with respect to severe infarction (0.9±0.8 and 0.8±1.1 versus 1.4±1.5) and wall thinning-both overall wall thinning (1.5±1.2 and 1.4±1.1 versus 2.3±1.7) and severe wall thinning (0.50±0.8 and 0.4±0.7 versus 0.9±1.1) (Table 2, lines 1-4, FIG. 3). In summary, treatment with the CardioMatrix in this rat AMI model not only improves ventricular function but also reduces the severity and hence, the size of the infarcts as well as the amount of wall thinning present after 28 days.

TABLE 2

Pathology results. The mean and SDs are calculated per parameter; the values shown in bold are pictured in FIG. 3.

| II. Pathology (slices/rat) | 3% CardioMatrix mean ± SD | 1% CardioMatrix mean ± SD | Control mean ± SD |
|---|---|---|---|
| 1. Infarction present | 2.6 ± 1.4 | 3.0 ± 1.3 | 3.1 ± 2.0 |
| 2. Severe Infarction | 0.9 ± 0.8 | 0.8 ± 1.1 | 1.4 ± 1.5 |
| 3. Wall thinning | 1.5 ± 1.2 | 1.4 ± 1.1 | 2.3 ± 1.7 |
| 4. Severe wall thinning | 0.5 ± 0.8 | 0.4 ± 0.7 | 0.9 ± 1.1 |
| 5. Fibrosis present | 2.6 ± 0.7 | 3.0 ± 1.7 | 3.1 ± 2.1 |
| 6. Inflammation present | 2.9 ± 0.8 | 2.8 ± 1.5 | 3.3 ± 1.9 |

Discussion of Results

In this example, improved cardiac function as measured by echocardiography demonstrated the efficacy of an CardioMatrix material of the present inventions in a rat animal model of AMI. Additionally, histological characterization of the CardioMatrix material effects compared to the vehicle control further supports the therapeutic benefit of the CardioMatrix material with respect to smaller infarct sizes and less wall thinning in treated animals. Specifically, improved recovery of left ventricular contractility after experimental infarction was seen in the high-dose 3% CardioMatrix group compared with the vehicle control group (+7.0% versus −0.6%, p=0.04) with an intermediate response in the low-dose 1% CardioMatrix group (+2.2%). Despite similar areas of myocardium at risk in the 3 groups, indicated by similar LVEFs at day 3 and similar number of cardiac slices per rat with fibrosis, inflammation and infarction at day 28, there was a reduction of the size of infarct and wall thinning in the CardioMatrix groups compared to the control group.

It has been reported that endothelial-cardiac myocyte interactions play a key role in cardiac regulation (6). (17).). It is believed, without being held to theory, that the scaffold formed by the CardioMatrix material provide an angiogenic environment (e.g., a myocardial microenvironment) that promotes cell engraftment, long-term cell survival and vascular structure formation (e.g., a capillary-like network formation).

It has been reported (14) that injection of an SAP alone in their rat AMI model did not statistically improve ventricular fractional shortening or lessen infarct size. However, the results of the present example demonstrate that a statistically significant ventricular recovery is seen when the results for the 3% CardioMatrix used was compared to the vehicle control (p=0.04).

It is believed, without being held to theory, that on a cellular level, the creation of nanofiber scaffold micro-environments, via injection of a CardioMatrix according to various embodiments of the present inventions, can promote cardiomyocyte and endothelial cell survival and organization after ischemic injury (5) and result in improvement in recovery of ventricular contractility. In addition, the results demonstrate that in various embodiments of the inventions can promote protection against reperfusion injury or a cardioprotective effect. It is believed, without being held to theory, that the L-arginine (LA) peptide sequence present in the CardioMatrix of this example can promote or provide a cardioprotective effect. For example, nitric oxide (NO) can be formed from LA and oxygen and NO is synthesized in response to physiological and pathological stimuli; as cardiac reperfusion injury has been attributed to reduced NO activity resulting from deficiency of LA (3), various embodiments of the present inventions can provide a treatment via local delivery of NO. In addition to heart disease, several other diseases have been linked to inappropriate release of nitric oxide including hypertension, septic shock, neuro-degeneration, arthritis, and asthma. Accordingly, in various embodiments, the present inventions provide methods for the treatment of one or more of hypertension, septic shock, neuro-degeneration, arthritis, and asthma using local administration of a LA containing CardioMatrix.

It is believed, without being held to theory, that administration of LA via a CardioMatrix material to cardioplegic solutions or use during reperfusion of the heart can facilitate the return of left ventricle function after hypothermic ischemia through the increase in the release of nitric oxide and preservation of endothelial cells function (18). Accordingly, in various embodiments, the present inventions include methods for facilitating the return of ventricle function by local administration of a substantially cell free solution containing greater than about 1% CardioMatrix by weight, and preferably greater than about 3% CardioMatrix by weight.

It is also believed, without being held to theory, that another mechanism by which the present inventions act, is by enhancement of endothelial and myocyte-like precursor cell growth, resulting in mature microvascular environments. It has been reported that such enhancement can facilitate healing (5). It is believed, without being held to theory, that differences in the cell types or time-course of populating the nanofiber scaffold microenvironments are mechanisms of action that can be used to explain the trend for greater improvement in contractility with the high-dose 3% CardioMatrix group compared with the 1% CardioMatrix group, despite similar areas of infarction and wall thinning.

It is also believed, without being held to theory, that in the present example the CardioMatrix material could be "rescuing" the damaged tissue by keeping it in a stunned state until the edema and inflammation subside (19, 22). The CardioMatrix also could be acting as a bulking agent that protects the tissue from wall stress which would further compromises cardiac function (19). Since wall stress is an important surrogate marker for congestive heart failure, it is believed that the present inventions provide a biomechanical or biophysical protective effect towards the infracted tissue (19).

Example 2

Studies: Biocompatability and Toxicology

Standard in vitro toxicology studies, including EN/ISO tests for cytotoxicity and hemocompatibility, have been completed. The tests below were completed at a FDA certified toxicology testing company (Toxikon Corp, Bedford, Mass.) using established standards of measure on a CardioMatrix material (Tables 3 and 4). The CardioMatrix solution tested in this example comprised various concentrations of CardioMatrix powder in substantially sucrose free aqueous solution.

TABLE 3

In vivo biocompatibility and toxicology tests.

| TEST | *RESULT |
|---|---|
| Cytotoxicity: Agar Diffusion ISO 10993-5 | Non-cytotoxic |
| Hemolysis: Direct Contact (ISO 10993-4) | Non-hemolytic |
| Prothrombin Time Assay: | No adverse effect on prothrombin coagulation Human Plasma (ISO 10993-4) |

*These tests are contract to the FDA certified commercial toxicology test facility (Toxikon Corp, Bedford, MA.).

TABLE 4

In vivo animal studies

| TEST | *RESULT |
| --- | --- |
| ADME Tox: 14 day implant | No problematic organ accumulation, excretion. 14C Radiolabeled CardioMatrix 10% excreted by day 14 |
| Rabbit Muscle Implant: 14 day (ISO 10993-6) | Non-toxic score across 13 categories of reactions |
| Rabbit Pyrogenicity: 24 hour (ISO-10993-11) | No effect on animals |
| Intracutaneous Implant: 72 hours (ISO 10993-12) | Primary Irritation Index = 0.0 "Negligible" No febrile reaction from any animal over 24 hours after intravenous injection of dilute solution |
| CNS Lesions in Hamsters: 2-60 days | Reduced scarring and reinnervation across the severed optic tract caudal to the lesion only in CardioMatrix treated animals |

Cytotoxicity

The Agar Diffusion test (ISO 10993-5) measures a material's effect on cell cultures, which are extremely sensitive to minute quantities of leachable chemicals and readily display characteristic signs of toxicity in the presence of potentially harmful leachables. The biological reactivity of a mammalian monolayer, L929 mouse fibroblast cell culture, in response to the test article was determined as "no-reactivity" in tests.

Hemolysis

The hemolysis test (Direct Contact, ISO-10993-4) measures the ability of a material to cause red blood cells to rupture. This test is derived from well-established NIH protocols and is performed in triplicate. This test uses rabbit blood in direct contact with the test material and the degree of hemolysis is measured spectrophotometrically. The CardioMatrix tested "non-hemolytic" in tests carried out by an independent FDA-certified testing agency.

Coagulation Prothrombin Time

Prothrombin Time (Human Plasma, ISO 10993-4) measures the effect of a test article extract on human blood coagulation time. This assay has become a suitable clinical means of determining the presence and functioning ability of prothrombin in the process of coagulation. The CardioMatrix did not have an adverse effect on prothrombin coagulation time of human plasma, in tests carried out by an independent FDA-certified testing agency.

ADME and Biodegradability

To measure the local and whole animal distribution a 14C, carbon radiolabeled version of a Cardiomatrix was generated. The radiolabeled version was internally labeled at the third alanine site (Acetyl-(RADA)-(R-[$^{14}$C(U)-Ala]-D-A)-(RADA)$_2$-CONH$_2$) as opposed to a labeled acetyl group which could be cleaved off, in order to better characterize the adsorption, degradation, metabolism and excretion (ADME) of the CardioMatrix material in vivo. The radiolabeled material was then implanted into Sprague Dawley rats in a femur defect model. Urine and stool samples were collected and the radioactivity was counted.

Rabbit Muscle Implant (2 Weeks)

This test assesses the local effects of material on contact with living tissue. Test article was implanted into paravertebral muscle of 3 New Zealand white rabbits, with negative control (GelFoam) implanted in the contralateral muscle of each animal. Healing was allowed for 2 weeks. Animals were sacrificed and implants excised. Excised implants were examined macroscopically with a magnifying lens and fixed in formalin. Histologic slides of hematoxylin and eosin (H&E) and Mason's Trichrome stained sections were prepared, studied microscopically by a board-certified veterinary pathologist, and evaluated on a scale of 0-3. CardioMatrix implants retained the initial implant volume, collagen fibers, and vascularization of the injection site. It was rated Non-Toxic (0.13) on a scale ranging from Nontoxic (<1), Slightly Toxic (1 to <2), Mildly Toxic (2 to <3), Moderately Toxic (3 to >4), to Severely Toxic (<4), in tests carried out by an independent FDA-certified testing agency.

Intracutaneous Reactivity

Irritation reactivity tests assess the localized reaction of tissues, including breached tissue and blood contact, to device materials or extracts. A 0.5% w/v peptide CardioMatrix solution was extracted in NaCl and CSO at a ratio of 0.2 gm per 1.0 mL at 70±2° C. for 24 hours. Control extracts were prepared, in a similar manner to the test article. Three rabbits were injected intracutaneously, using one side of the animal for the test article extracts and the other side for the control extracts, at 0.2 mL per site. The injected sites were examined at 24, 48, and 72 hours post inoculation for gross evidence of tissue reaction such as erythema, edema, and necrosis. A Primary Irritation Index of 0.5 or less will be considered a negligible irritant, where 0.5 to <2 are slight irritants, 2 to <5 are moderate irritants, and >5 are severe irritants. The test sites injected with CardioMatrix did not exhibit signs of erythema or edema through the 72 hour observation point. The Primary Irritation Index for the material is 0.0, in tests carried out by an independent FDA-certified testing agency.

Rabbit Pyrogen

The purpose of the test was to detect the risk of a patient to a febrile reaction as a result of the administration of the test article extract. The test article was prepared by mixing 9 ml of the test article with 9 mL of 0.9% USP Sodium Chloride for Injection (NaCl) and the resulting gel extracted at a ration of 0.2 gm per 1.0 mL. The test article extract was administered by intravenous injection at 10 mL/kg. The rectal temperatures of the injected rabbits were compared with the temperature of a control rabbit similarly injected with 0.9% USP Sodium Chloride for Injection (NaCl). The base-line temperatures of the rabbits, determined no more than 30 minutes prior to injection of the test article extract, were used to exclude rabbits whose body temperatures vary by more than 1° C. from each other and whose temperatures are greater than 39.8° C. Body temperatures were recorded at 30 minute intervals between 1 and 3 hours subsequent to injection. If no rabbit exhibited a rise in temperature of 0.5° C. or more about its base-line temperature, the product met the requirements for the absence of pyrogens. None of the animals injected with the test article extract exhibited signs of pyrogenic response, in tests carried out by an independent FDA-certified testing agency.

The section headings used herein are for organizational purposes only and are not to be construed as limiting the subject matter described in any way.

While the present inventions have been described in conjunction with various embodiments and examples, it is not intended that the present inventions be limited to such embodiments or examples. On the contrary, the present inventions encompass various alternatives, modifications, and equivalents, as will be appreciated by those of skill in the art.

While the inventions have been particularly shown and described with reference to specific illustrative embodiments, it should be understood that various changes in form and detail may be made without departing from the spirit and scope of the present inventions. Therefore, all embodiments that come within the scope and spirit of the present inventions, and equivalents thereto, are claimed.

References

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls.

1. Assmus B, Honold J, Schachinger V, Britten M B, Fischer-Rasokat U, Lehmann R, Teupe C, Pistorius K, Martin H, Abolmaali N D, Tonn T, Dimmeler S, and Zeiher A M. Transcoronary transplantation of progenitor cells after myocardial infarction. *N Engl J Med* 355: 1222-1232, 2006.
2. Braunwald E and Bristow M R. Congestive heart failure: fifty years of progress. *Circulation* 102: IV14-23, 2000.
3. Brunner F, Maier R, Andrew P, Wolkart G, Zechner R, and Mayer B. Attenuation of myocardial ischemia/reperfusion injury in mice with myocyte-specific overexpression of endothelial nitric oxide synthase. *Cardiovasc Res* 57: 55-62, 2003.
4. Chien K R. Lost and found: cardiac stem cell therapy revisited. *J Clin Invest* 116: 1838-1840, 2006.
5. Chung T, Emmett L, Khoury V, Lau G T, Elsik M, Foo F, Allman K C, and Kritharides L. Atrial and ventricular echocardiographic correlates of the extent of pulmonary embolism in the elderly. *J Am Soc Echocardiogr* 19: 347-353, 2006.
6. Darland D C, D'Amore P A. Cell-cell interactions in vascular development. *Curr Top Dev Biol:* 107-149, 2001
7. Davis M E, Hsieh P C, Takahashi T, Song Q, Zhang S, Kamm R D, Grodzinsky A J, Anversa P, and Lee R T. Local myocardial insulin-like growth factor 1 (IGF-1) delivery with biotinylated peptide nanofibers improves cell therapy for myocardial infarction. *Proc Natl Acad Sci USA* 103: 8155-8160, 2006.
8. Davis M E, Motion J P, Narmoneva D A, Takahashi T, Hakuno D, Kamm R D, Zhang S, and Lee R T. Injectable self-assembling peptide nanofibers create intramyocardial microenvironments for endothelial cells. *Circulation* 111: 442-450, 2005.
9. Engel F B, Hsieh P C, Lee R T, and Keating M T. FGF1/p38 MAP kinase inhibitor therapy induces cardiomyocyte mitosis, reduces scarring, and rescues function after myocardial infarction. *Proc Natl Acad Sci USA* 103: 15546-15551, 2006.
10. Genove, E, Shen C., Zhang S., and Semino, C E. The effect of functionalized self-assembling peptide scaffolds on human aortic endothelial cell function. *Biomaterials* 16: 3341-3351, 2005.
11. Hiramatsu T, Forbess J M, Miura T, Roth S J, Cioffi M A, and Mayer J E, Jr. Effects of endothelin-1 and L-arginine after cold ischemia in lamb hearts. *Ann Thorac Surg* 61: 36-40; discussion 40-31, 1996.
12. Hoch, R V and Soriano, P. Roles of PDGF in animal development *Development* 13); 4769-4784. 2003
13. Holmes T C, de Lacalle S, Su X, Liu G., Rich A., and Zhang S. Extensive neurite outgrowth and active synapse formation on self-assembling peptide scaffolds. *Proc Natl Acad Sci USA* 97: 6728-6733, 2000.
14. Hsieh P C, Davis M E, Gannon J, MacGillivray C, and Lee R T. Controlled delivery of PDGF-BB for myocardial protection using injectable self-assembling peptide nanofibers. *J Clin Invest* 116: 237-248, 2006.
15. Hsieh P C, MacGillivray C, Gannon J, Cruz F U, and Lee R T. Local controlled intramyocardial delivery of platelet-derived growth factor improves postinfarction ventricular function without pulmonary toxicity. *Circulation* 114: 637-644, 2006.
16. Jugdutt B I. Ventricular remodeling after infaction and extracellular collagen matrix: when is enough enough? *Circulation* 108: 1395-1403.
17. Narmoneva D A, Vukmirovic R, Davis M E, Kamm R D, and Lee R T. Endothelial cells promote cardiac myocyte survival and spatial reorganization: implications for cardiac regeneration. *Circulation* 110: 962-968, 2004.
18. Okonski P, Szram S M, Mussur M, Banach M., Fila M, Bielaski K, Kedziora J, and Zaslonka J. Effect of L-arginine on oxygen consumption and haemodynamic function of rat's heart exposed to cold cardioplegic ischaemia and reperfusion. *Ann Transplan* 7: 28-31, 2002.
19. Pfeffer M A and Braunwald E. Ventricular remodeling after myocardial infarction. Experimental observations and clinical implications. *Circulation* 81: 1161-1172, 1990.
20. Saint John-Sutton, M G, and Sharpe, N. Left ventricular remodeling after myocardial infaction: pathophysiology and therapy. *Circulation* 101: 2981-2988, 2000.
21. Stone G W, Grines C L, Cox D A, Garcia E, Tcheng J E, Griffin J J, Guagliumi G, Stuckey T, Turco M, Carroll J D, Rutherford B D, and Lansky A J. Comparison of angioplasty with stenting, with or without abciximab, in acute myocardial infarction. *N Engl J Med* 346: 957-966, 2002.
22. Sutton M G and Sharpe N. Left ventricular remodeling after myocardial infarction: pathophysiology and therapy. *Circulation* 101: 2981-2988, 2000.
23. Thijssen V L J L, Borgers M., Lenders M,-H, Ramaekers F S C, Suzuki G., Palka B., Fallavollita J A, Thomas S A, and Canty Jr. J M. Temporal and spatial variations in structural protein expression during the progression from stunned to hibernating myocardium. *Circulation* 110: 3313-3321.
24. Zhang S, Holmes T C, DiPersio C M, Hynes, R O, Su X, and Rich, A. Self-complementary oligopeptide matrices support mammalian cell attachment. *Biomaterials,* 18:1385-1393, 1995.
25. Zhang S, Zhao X, and Spirio L. PuraMatrix: Self-Assembling Nanofiber Scaffolds., In: *Scaffolding in Tissue Engineering,* Edited by Peter Ma and Jennifer Elisseeff, 217-240, 2005.

In accordance with 37 CFR 1.52(e)(5), a Sequence Listing in the form of a text file (entitled "2004837-0016_ST25.txt," created on Jan. 5, 2010, and 1 kilobyte) is incorporated herein by reference in its entirety.

What is claimed is:

1. A method for treating a cardiac condition comprising the steps of:
   providing a cell free solution consisting of:
      at least about 1% by weight of polypeptides with an amino acid sequence comprising RADARADARADARADA (SEQ. ID NO. 1); and
      a physiologically acceptable amount of sucrose; and
   administering by local injection into cardiac tissue a therapeutically effective amount of the cell free solution to a mammal having one or more of atrial fibrillation, acute myocardial infarction, valve disease, ischemia-reperfusion, pericardial disease, congenital heart disease, and congestive heart failure.

2. The method of claim 1, wherein the step of administering comprises administering the polypeptides in an amount sufficient to reduce one or more of infarct size, infarct expansion, ventricular wall stress, and atrial fibrillation.

3. The method of claim 1, wherein the cell free solution consists of at least about 3% by weight of polypeptides with an amino acid sequence comprising RADARADARADARADA (SEQ. ID NO. 1).

4. A method for treating an infarct comprising the steps of:
   providing a cell free solution consisting of:
      at least about 1% by weight of polypeptides with an amino acid sequence comprising RADARADARADARADA (SEQ. ID NO. 1); and
      a physiologically acceptable amount of sucrose; and
   injecting the cell free solution into the infarct.

5. A method for treating a cardiac condition comprising the steps of:
   providing a cell free solution consisting of:
      at least about 1% by weight of polypeptides with an amino acid sequence consisting of RADARADARADARADA (SEQ. ID NO. 1); and
      a physiologically acceptable amount of sucrose; and
   administering by local injection into cardiac tissue a therapeutically effective amount of the cell free solution to a mammal having one or more of atrial fibrillation, acute myocardial infarction, valve disease, ischemia-reperfusion, pericardial disease, congenital heart disease, and congestive heart failure.

6. The method of claim 5, wherein the step of administering comprises administering the polypeptides in an amount sufficient to reduce one or more of infarct size, infarct expansion, ventricular wall stress, and atrial fibrillation.

7. The method of claim 5, wherein the cell free solution consists of at least about 3% by weight of polypeptides with an amino acid sequence consisting of RADARADARADARADA (SEQ. ID NO. 1).

* * * * *

SEQUENCE LISTING

```
<160> NUMBER OF SEQ ID NOS: 1

<210> SEQ ID NO 1
<211> LENGTH: 16
<212> TYPE: PRT
<213> ORGANISM: Artificial Sequence
<220> FEATURE:
<223> OTHER INFORMATION: Self-Assembling Peptide sequence
```

```
<400> SEQUENCE: 1

Arg Ala Asp Ala Arg Ala Asp Ala Arg Ala Asp Ala Arg Ala Asp Ala
1               5                   10                  15
```